United States Patent [19]

Castanet et al.

[11] Patent Number: 5,194,676
[45] Date of Patent: Mar. 16, 1993

[54] CATALYST AND PROCESS FOR THE SYNTHESIS OF SATURATED CARBOXYLIC ESTERS

[75] Inventors: Yves Castanet, Hem; Christophe Legrand, Mons en Baroeul; Andre Mortreux; Francis Petit, Villeneuve D'Ascq, all of France

[73] Assignee: Atochem, Puteaux, France

[21] Appl. No.: 674,745

[22] Filed: Mar. 26, 1991

[30] Foreign Application Priority Data

Mar. 26, 1990 [FR] France .................. 90 03805

[51] Int. Cl.$^5$ ............................. C07C 67/38
[52] U.S. Cl. .................... 560/241; 560/232; 560/233
[58] Field of Search .............. 560/241, 232, 233

[56] References Cited

U.S. PATENT DOCUMENTS 3,213,155 10/1965 Schriesheim et al .............. 562/496
4,614,816 9/1986 Drury et al. ...................... 560/243
4,664,851 5/1987 Drent ............................... 560/234

FOREIGN PATENT DOCUMENTS 106656 4/1984 European Pat. Off. ............ 560/265

Primary Examiner—Arthur C. Prescott
Attorney, Agent, or Firm—Millen, White, Zelano and Branigan

[57] ABSTRACT

Saturated carboxylic esters are produced from alkyl formate and an olefin, without the presence of substantial amounts of carbon monoxide, at a temperature of 120° to 280° C., under a pressure of 1 to 3,000 bars, in the presence of a catalyst based on ruthenium coordinated by ligands selected from carbon monoxide, halogen atoms and amines, and in the presence of an amide as a solvent. The catalyst is selected from catalysts consisting essentially of $RuCl_3.3H_2O$; catalysts consisting essentially of the combination of an $RuCl_3.3H_2O$ together with at least one stabilizer selected from iodine, covalent iodides and quaternary ammonium halides; catalysts comprising $Ru_3(CO)_{12}$ together with at least one stabilizer such as is mentioned above; and catalysts selected from $RuI_3$, $[RuCl_2(CO)_3]_2$, $Ru(NH_3)_6Cl_3$ and $[Ru(NH_3)_5Cl]Cl_2$, comprising, where appropriate, in addition, at least one stabilizer such as is mentioned above.

20 Claims, No Drawings

CATALYST AND PROCESS FOR THE SYNTHESIS OF SATURATED CARBOXYLIC ESTERS

BACKGROUND OF THE INVENTION

The present invention relates to a family of catalysts and to a process for the synthesis of saturated carboxylic esters from alkyl formate and an olefin.

It is known that saturated carboxylic esters can be prepared by the reaction of alkyl formate and an olefin under pressure, at relatively high temperature and in the presence of a catalytic system comprising a transition metal derivative. For example, Patent EP-A-106,656 describes the reaction of methyl formate with ethylene in acetic acid as a solvent, at 200° C. and under a pressure of 25 bars, in the presence of a catalytic system comprising iridium trichloride, methyl iodide as a promoter and para-toluenesulphonic acid as a copromoter; after 30 minutes' reaction, the reaction mixture contains, on the one hand 10.5% of unconverted methyl formate, and on the other a mixture of products containing 12.7% of methyl propionate, thereby enabling the activity of the catalyst with respect to methyl propionate, defined as the number of moles of methyl formate converted to methyl propionate per mole of catalyst per hour, to be calculated as approximately 330 $h^{-1}$. In this process, not only is the selectivity for methyl propionate very low, but also the scarcity and cost of iridium make the synthesis of methyl propionate uneconomical. The publication by W. KEIM and J. BECKER in Journal of Molecular Catalysis, 54 (1989) 95-101 describes the same reaction performed for 20 hours at 230° C. at 90 bars in toluene in the presence of $Ru_3(CO)_{12}$ as a catalyst: under these conditions, the conversion is 100% and the selectivity for methyl propionate 92%, thereby enabling the activity of the catalyst with respect to methyl propionate, as defined above, to be calculated as 230 $h^{-1}$. This technique represents an advance with respect to that of Patent EP-A-106,656, inasmuch as an excellent selectivity may be obtained by means of a ruthenium catalyst which is more readily available commercially than that of iridium. However, the activity of the catalyst with respect to methyl propionate remains moderate, and even less than that of the patent already cited.

HIDAI et al. have published, in Journal of Molecular Catalysis, 40 (1987) 243-254, the reaction, performed in the presence of various catalytic systems based on ruthenium and iodides, of ethylene with an equimolar mixture of carbon monoxide and methanol. The publication shows that, at 190° C. and in the presence of $Ru_3(CO)_{12}$ as a catalyst, the best results are obtained using sodium iodide or lithium iodide as a promoter in preference to phenyl iodide, tetra-n-butylammonium iodide or tetraphenylphosphonium iodide. The selectivity is good and the catalytic activity with respect to methyl propionate increases with the mole ratio of sodium iodide to ruthenium, being capable of reaching 1220 $h^{-1}$ when the I/Ru ratio is equal to 10. This process has, however, two serious drawbacks: on the one hand the reaction necessitates recourse to gaseous carbon monoxide, the handling and transport of which are dangerous, thereby having the effect of limiting the production of methyl propionate to locations in proximity to industrial sites producing this gas; and on the other hand the use of large quantities of iodides is a well-known cause of corrosion of the steel reactors in which the reaction would be carried out.

SUMMARY OF THE INVENTION

A first object of the present invention is to provide a catalyst and a process which are capable of producing methyl propionate with a high selectivity and a high catalytic activity from a starting material while avoiding recourse to carbon monoxide. A second object of the present invention is to provide a catalyst enabling methyl propionate to be produced with a high selectivity and a high activity without having recourse to large quantities of iodides, so as to limit the risks of corrosion of the reactors.

Upon further study of the specification and appended claims, further objects and advantages of this invention will become apparent to those skilled in the art.

The present invention is based on the discovery that these two problems may be solved simultaneously by performing the synthesis of methyl propionate from methyl formate and ethylene, without the presence of substantial amounts of carbon monoxide, at a temperature of 120° to 280° C. approximately— preferably 160° to 250° C.—under a pressure of 1 to 3,000 bars—preferably 20 to 200 bars—in the presence of a catalyst based on ruthenium coordinated by ligands selected from carbon monoxide, halogen atoms and amines, and in the presence of an amide as a solvent. In addition, it was discovered that these reaction conditions may be applied successfully to the synthesis of saturated carboxylic esters from alkyl formate and olefin according to the reaction:

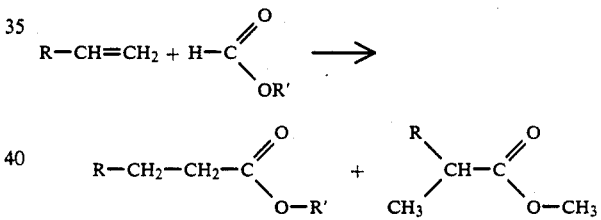

in which R is selected from a hydrogen atom and alkyl radicals preferably having 1 to 8 carbon atoms and R' denotes an alkyl radical preferably possessing 1 to 8 carbon atoms. In the case of methyl formate and ethylene, the process according to the invention enables methyl propionate to be obtained with a very high activity and, as a result of the strong selectivity, enables it to be isolated very easily from the reaction medium.

The catalyst used in the process according to the invention is based on ruthenium coordinated by halogen atoms and/or molecules of carbon monoxide or of amines such as, for example, ammonia, propylamine, triethylamine, piperidine or ethylenediamine. It forms a complex which can be mono-, bi- or trimetallic. Preferably, such a catalyst comprises at least one halogen atom as a ligand. Examples of such catalysts comprise, for example, ruthenium trichloride $RuCl_3.3H_2O$, ruthenium iodide $RuI_3$, bis(dichlorotricarbonylruthenium) $[RuCl_2(CO)_3]_2$ and tris(tetracarbonylruthenium) $Ru_3(CO)_{12}$, as well as the compounds $Ru(NH_3)_6Cl_3$ and $[Ru(NH_3)_5Cl]Cl_2$. Where appropriate, the catalyst can comprise ligands other than a halogen atom or carbon monoxide, with the exception, however, of phosphines, whose presence in substantial quantities is inadvisable since it strongly decreases the catalytic activity, except in the presence of iodine in excess quantities relative to the phosphine.

The process according to the invention may be carried out in the presence, in addition, of iodine, of a covalent iodide or of a quaternary ammonium halide playing the part, not necessarily of a promoter of the catalytic activity, but of a stabilizer of the active catalytic species. As examples of covalent iodides, methyl, hydrogen, ethyl, n-butyl and phenyl iodides may be mentioned. As examples of quaternary ammonium halides, tetraethylammonium iodide and tetra-n-butylammmonium chloride may be mentioned. The mole ratio of iodine, the covalent iodide or the quaternary ammonium halide relative to the ruthenium-based catalyst is preferably between 0.5 and 6 approximately, and more especially between 1 and 2.5. The addition of quaternary phosphonium halide is inadvisable since it decreases the catalytic activity.

The mole ratio of the alkyl formate to ruthenium in the process according to the invention is preferably between 500 and 10,000 approximately. The alkyl formate and the olefin are, on the other hand, in a substantially equimolar ratio. The reaction according to the invention is preferably performed in solution in an amide, since recourse to other tested solvents (toluene, acetone, tetrahydrofuran) has proved to be relatively ineffective. As examples of amides capable of being used, there may be mentioned, in particular, N-methylpyrrolidone, dimethylacetamide, formamide, methylformamide and dimethylformamide, the latter being preferred. The quantity of solvent may be selected within a wide range, on the understanding that, where the results are equivalent, the aim will be to use the smallest possible quantity of solvent so as to simplify the problems of separation of the saturated carboxylic ester formed at the end of the reaction. As a general rule, at least 0.5 volume, preferably 1 to 2 volumes and at most 3 volumes approximately, of amide is/are used per volume of alkyl formate (it being recalled, for example, that at atmospheric pressure, methyl formate is a liquid having a boiling point equal to 33° C.).

It is important that the reaction according to the invention be performed without the presence of substantial amounts of carbon monoxide, since it has been observed that the addition of carbon monoxide to the reaction mixture has the result of decreasing the catalytic activity. In general, the presence of up to approximately 10% by volume of carbon monoxide relative to ethylene, and preferably up to approximately 5% by volume, may be tolerated. Proportions of carbon monoxide larger than these values will be considered, according to the present invention, to be the presence of a substantial amount of carbon monoxide.

The reaction according to the invention is preferably performed without the presence of a substantial amount of water, since the presence of water has the result of decreasing the catalytic activity. In general, the presence of water in a mole ratio ranging up to approximately 20 relative to the ruthenium may be tolerated.

The reaction pressure and temperature, selected within the ranges stated above, are naturally dependent on one another, and may be determined by those skilled in the art in accordance with the technology adopted (reactor type, means of compression, and the like) with a view to optimizing the efficiency of the reaction, in particular the catalytic activity, for each catalyst.

The reaction time is naturally dependent on the selected pressure and temperature, and will increase proportionately as the latter are lowered. Within the pressure and temperature ranges stated above, a sufficient reaction time to convert virtually all of the alkyl formate is generally between 2 minutes and 10 hours.

When the olefin used in the process according to the invention comprises more than 2 carbon atoms (R is an alkyl radical having from 1 to 8 carbon atoms), the reaction leads to the formation of a mixture of linear and branched isomers of the saturated carboxylic ester. In general, the reaction favors the formation of one of the isomers in the mixture, and it is within the capacity of those skilled in the art to select one of the catalytic systems described above for the purpose of preferentially preparing one of these isomers.

The technology necessary for the industrial implementation of this type of reaction is well known to those skilled in the art. At the end of the reaction, the reaction mixture is generally discharged from the reactor and subjected to a flash distillation for the purpose of removing the mixture of saturated carboxylic ester(s) and unconverted alkyl formate, from which the desired products are separated in a distillation column while the amide and the catalyst are recycled to the reactor.

Among the catalysts proposed by the present invention for the synthesis of saturated carboxylic esters from alkyl formate and an olefin, some had never been proposed for this reaction. This applies to:

a catalyst consisting essentially of ruthenium trichloride $RuCl_3.3H_2O$, and especially consisting of no other component apart from possible impurities;

a catalyst consisting essentially of the combination of a ruthenium trichloride $RuCl_3.3H_2O$ together with at least one stabilizer selected from iodine, covalent iodides and quaternary ammonium halides, and especially consisting of no component other than possible impurities;

a catalyst comprising tris(tetracarbonylruthenium) $Ru_3(CO)_{12}$ together with at least one stabilizer selected from iodine, covalent iodides and quaternary ammonium halides, and which can optionally comprise other catalytic components;

a catalyst selected from ruthenium iodide $RuI_3$, bis(dichlorotricarbonylruthenium) $[RuCl_2(CO)_3]_2$ and the compounds $Ru(NH_3)_6Cl_3$ and $[Ru(NH_3)_5Cl]Cl_2$, which can optionally comprise, in addition, at least one stabilizer selected from iodine, covalent iodides and quaternary ammonium halides and other catalytic components.

The present invention makes possible a simple and effective preparation of saturated carboxylic esters such as methyl propionate (from ethylene) and methyl butyrate and isobutyrate (from propene), the latter being of special importance on account of the possibility of dehydrogenating it to methyl methacrylate.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding French application 90.03805, are hereby incorporated by reference.

EXAMPLES

Example 1

0.11 millimole of ruthenium trichloride $RuCl_3.3H_2O$ and 0.25 millimole of tetraethylammonium iodide in 30 cm$^3$ of degassed dimethylformamide are mixed under nitrogen in a Schlenk tube. This catalytic system is transferred to a 100-cm$^3$ autoclave reactor equipped with a mechanical stirrer and purged beforehand with nitrogen. Ethylene is introduced into this reactor to a pressure of 55 bars at 20° C., then, while stirring is maintained, the mixture is heated to 190° C. and, when this temperature is reached, 0.26 mole of methyl formate (16 cm$^3$) is introduced by means of an injection pump under pressure. After reaction for one hour, the reactor is allowed to cool and the reaction mixture is recovered and analysed by gas chromatography. The degree of conversion C of methyl formate, as well as the selectivity S for methyl propionate in the products formed and the activity A expressed in h$^{-1}$, defined as the number of moles of methyl formate converted to methyl propionate per mole of catalyst (Ru) per hour, are shown in the table below.

Example 2

The experimental procedure of Example 1 is reproduced, modifying the temperature: 180° C. instead of 190° C. The results are shown in the table below.

Examples 3 to 8

The experimental procedure of Example 1 is reproduced, replacing tetraethylammonium iodide by another iodine compound:
  phenyl iodide (Example 3),
  hydrogen iodide (Example 4),
  iodine (Example 5), the reaction time being extended to 2 hours in this case,
  methyl iodide (Example 6),
  ethyl iodide (Example 7),
  1-iodobutane (Example 8).
The results are shown in the table below.

Example 9 (Comparative)

The experimental procedure of Example 6 is reproduced, adding 0.11 millimole of triphenylphosphine, capable of playing the part of a ligand for the ruthenium, to the reaction medium. The results are shown in the table below.

Example 10

The experimental procedure of Example 5 is reproduced, adding 0.25 millimole of triphenylphosphine, capable of playing the part of a ligand for the ruthenium, to the reaction medium. The results are shown in the table below.

Example 11 (Comparative)

The procedure of Example 10 is reproduced, with the exception of the quantity of triphenylphosphine, which is increased to 1 millimole. The results are shown in the table below.

Example 12 (Comparative)

The experimental procedure of Example 1 is reproduced, replacing triethylammonium iodide by methyltriphenylphosphonium iodide. The results are shown in the table below.

Example 13

The experimental procedure of Example 1 is reproduced, adding a pressure of 3 bars of carbon monoxide in the reactor. The results are shown in the table below.

Example 14 (Comparative)

The procedure of Example 13 is reproduced, with the exception of the carbon monoxide pressure in the reactor, which is increased to 30 bars, while the ethylene pressure is lowered to 30 bars. The results are shown in the table below.

Example 15

The experimental procedure of Example 1 is reproduced, apart from the following exceptions:
  ethylene is replaced by propene,
  the pressure in the reactor is increased to 100 bars,
  the temperature in the reactor is lowered to 160° C.
After reaction for 6 hours, a mixture of methyl butyrates in which the mole ratio $$\frac{\text{branched}}{\text{normal}}$$

is equal to 1.22 is obtained in a 31% yield.

Example 16

The experimental procedure of Example 6 is reproduced, replacing ruthenium trichloride by bis(dichlorotricarbonylruthenium) $[RuCl_2(CO)_3]_2$. The results are shown in the table below.

Example 17

The experimental procedure of Example 16 is reproduced, replacing methyl iodide by tetraethylammonium iodide. The results are shown in the table below.

Example 18

The experimental procedure of Example 1 is reproduced, replacing ruthenium trichloride by tris(tetracarbonylruthenium) $Ru_3(CO)_{12}$. The results are shown in the table below.

Example 19

The experimental procedure of Example 1 is reproduced, replacing ruthenium trichloride by ruthenium triiodide and tetraethylammonium iodide by tetra-n-butylammonium chloride. The results are shown in the table below.

Examples 20 and 21

The experimental procedure of Example 4 is reproduced, decreasing the quantity of hydrogen iodide, which is lowered to 0.06 millimole (Example 20) and 0.13 millimole (Example 21), respectively. The results are shown in the table below.

Example 22

The experimental procedure of Example 1 is reproduced, adding 0.5 millimole of water into the reactor from the start. The results are shown in the table below.

Example 23

The experimental procedure of Example 2 is reproduced, apart from the following exceptions:

methyl formate is introduced into the reactor while cold, before the ethylene,
the reaction is continued for 2 hours.
The results are shown in the table below.

Example 24 (Comparative)

The experimental procedure of Example 5 is reproduced, apart from the following two exceptions:
dimethylformamide is replaced by toluene,
the reaction time is increased to 10 hours.
At the end of this reaction time, analysis of the medium does not reveal the presence of any trace of methyl propionate.

Example 25

The experimental procedure of Example 1 is reproduced, introducing 1 cm$^3$ of deuterated methanol CD$_3$OD into the reactor at the same time as the methyl formate. The result obtained is identical to that of Example 1, and analysis of the medium does not reveal the presence of any trace of deuterated methyl propionate, thereby demonstrating that methanol does not play any part in the mechanism of formation of the propionate from methyl formate.

Example 26

The experimental procedure of Example 1 is reproduced, apart from the following two exceptions:
ruthenium trichloride is replaced by the compound Ru(NH$_3$)$_6$Cl$_3$;
the reaction temperature is lowered to 170° C.
The results are shown in the table below.

Example 27

The experimental procedure of Example 1 is reproduced, replacing ruthenium trichloride by the compound [Ru(NH$_3$)$_5$Cl]Cl$_2$.
The results are shown in the table below.

TABLE

| Example | C (%) | S (%) | A (h$^{-1}$) |
|---|---|---|---|
| 1 | 77 | 84 | 1530 |
| 2 | 43 | 91 | 920 |
| 3 | 77 | 84 | 1530 |
| 4 | 66 | 92 | 1440 |
| 5 | 61 | 88 | 635 |
| 6 | 65 | 94 | 1440 |
| 7 | 65.5 | 93 | 1440 |
| 8 | 71 | 94 | 1580 |
| 9 | 35 | 59 | 490 |
| 10 | 50 | 85 | 1000 |
| 11 | 6 | 46 | 65 |
| 12 | 71 | 14 | 235 |
| 13 | 36 | 87 | 730 |
| 14 | 45 | 11 | 120 |
| 16 | 52 | 87 | 1060 |
| 17 | 66 | 96 | 1490 |
| 18 | 34.5 | 97 | 790 |
| 19 | 50.5 | 92 | 1100 |
| 20 | 56 | 78 | 1030 |
| 21 | 66 | 87 | 1360 |
| 22 | 65 | 67 | 1030 |
| 23 | 86 | 97 | 980 |
| 26 | 31 | 91 | 670 |
| 27 | 35 | 96 | 800 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the synthesis of saturated carboxylic esters comprising reacting alkyl formate and an olefin, in the presence of up to 10% by volume of carbon monoxide, at a temperature of 120° to 280° C., under a pressure of 1 to 3,000 bars, in the presence of a catalytic amount of a catalyst based on ruthenium coordinated by ligands selected from carbon monoxide, halogen atoms and amines, and in the presence of an amide as a solvent.

2. A process according to claim 1 for the synthesis of methyl propionate, wherein the alkyl formate is methyl formate and the olefin is ethylene.

3. A process according to claim 1, wherein the mole ratio of alkyl formate to ruthenium is between 500 and 10,000.

4. A process according to claim 1, carried out in the further presence of iodine, of a covalent iodide or of a quaternary ammonium halide.

5. A process according to claim 4, wherein the mole ratio of iodine or of said covalent iodide or quaternary ammonium halide relative to ruthenium is between 0.5 and 6.

6. A process according to claim 1, wherein the solvent is dimethylformamide.

7. A process according to claim 3, characterized in that the amide is used in the proportion of 0.5 to 3 volumes per volume of alkyl formate.

8. A process according to claim 1, wherein the reaction between the alkyl formate and the olefin is performed for a time between 2 minutes and 10 hours.

9. A process according to claim 1, wherein the alkyl formate and the olefin are reacted in a substantially equimolar ratio.

10. A process according to claim 1, wherein the catalyst is:

(a) a catalyst consisting essentially of ruthenium trichloride RuCl$_3$.3H$_2$O;

(b) a catalyst consisting essentially of the combination of a ruthenium trichloride RuCl$_3$.3H$_2$O together with a stabilizing amount of at least one stabilizer selected from iodine, covalent iodides and quaternary ammonium halides;

(c) a catalyst comprising tris(tetracarbonylruthenium) Ru$_3$(CO)$_{12}$ together with a stabilizing amount of at least one stabilizer selected from iodine, covalent iodides and quaternary ammonium halides; or (d) a catalyst selected from ruthenium iodide RuI$_3$, bis(dichlorotricarbonylruthenium) [RuCl$_2$(CO)$_3$]$_2$ and the compounds Ru(NH$_3$)$_6$Cl$_3$ and [Ru(NH$_3$)$_5$Cl]Cl$_2$, comprising optionally in addition, a stabilizing amount of at least one stabilizer selected from iodine, covalent iodides and quaternary ammonium halides.

11. A process according to claim 10, wherein the reaction is conducted in the presence of up to 5% by volume of carbon monoxide.

12. A process according to claim 10, wherein the catalyst is (a).

13. A process according to claim 10, wherein the catalyst is (b).

14. A process according to claim 10, wherein the catalyst is (c).

15. A process according to claim 10, wherein the catalyst is (d).

16. A process according to claim 13, wherein methyl formate and ethylene are reacted in dimethylformamide as the solvent.

17. A process according to claim 16, carried out in the further presence of iodine, of a covalent iodine or of a quaternary ammonium halide.

18. A process according to claim 17, wherein the reaction is conducted in the presence of up to 5% by volume of carbon monoxide.

19. A process according to claim 1, wherein said reacting of alkyl formate and an olefin is conducted in a starting reaction milieu consisting essentially of said alkyl formate; said olefin; up to 10% by volume of carbon monoxide; a catalytic amount of a catalyst based on ruthenium coordinated by at least one ligand selected from the group consisting of carbon monoxide, a halogen atom, and an amine; an amide solvent; and, optionally, a stabilizing amount of at least one stabilizer selected from the group consisting of iodine, covalent iodide, and quaternary ammonium halide.

20. A process according to claim 19 wherein the solvent is dimethyl formamide.

* * * * *